(12) United States Patent
Drevik et al.

(10) Patent No.: US 6,929,629 B2
(45) Date of Patent: *Aug. 16, 2005

(54) ABSORBENT ARTICLE WITH IMPROVED FIT

(75) Inventors: Solgun Drevik, Mölnlycke (SE); Fredrik Asp, Onsala (SE)

(73) Assignee: SCA Hygiene Products AB, Gothenburg (SE)

(*) Notice: Subject to any disclaimer, the term of this patent is extended or adjusted under 35 U.S.C. 154(b) by 446 days.

This patent is subject to a terminal disclaimer.

(21) Appl. No.: 10/125,423

(22) Filed: Apr. 19, 2002

(65) Prior Publication Data

US 2002/0165512 A1 Nov. 7, 2002

Related U.S. Application Data

(60) Provisional application No. 60/284,871, filed on Apr. 20, 2001.

(51) Int. Cl.[7] .............................................. A61F 13/20
(52) U.S. Cl. .............. 604/385.31; 604/367; 604/385.01
(58) Field of Search ...................... 604/385.01, 385.23, 604/385.31, 367, 378

(56) References Cited

U.S. PATENT DOCUMENTS

| | | | |
|---|---|---|---|
| 3,294,091 A | 12/1966 | Morse | |
| 4,285,343 A | 8/1981 | McNair | |
| 4,608,047 A | 8/1986 | Mattingly | |
| 4,655,759 A | 4/1987 | Romans-Hess et al. | |
| 4,804,380 A | 2/1989 | Lassen et al. | |
| 5,730,737 A | 3/1998 | Widlund et al. | |
| 6,198,019 B1 * | 3/2001 | Hansson et al. | 604/378 |
| 6,425,890 B1 * | 7/2002 | Samuelsson et al. | 604/385.17 |
| 6,492,574 B1 * | 12/2002 | Chen et al. | 604/378 |
| 6,565,547 B2 * | 5/2003 | Bissah et al. | 604/385.01 |
| 6,592,561 B2 * | 7/2003 | Simard et al. | 604/385.04 |
| 6,740,069 B2 * | 5/2004 | Drevik | 604/385.01 |
| 2001/0039407 A1 * | 11/2001 | Widlund | 604/385.01 |
| 2002/0052589 A1 * | 5/2002 | Strand | 604/385.01 |
| 2002/0065497 A1 * | 5/2002 | Kolby-Falk | 604/368 |
| 2002/0068915 A1 * | 6/2002 | Drevik et al. | 604/385.01 |
| 2002/0156443 A1 * | 10/2002 | Drevik et al. | 604/385.01 |
| 2002/0156450 A1 * | 10/2002 | Drevik et al. | 604/385.101 |
| 2002/0165513 A1 * | 11/2002 | Drevik et al. | 604/385.01 |

FOREIGN PATENT DOCUMENTS

| | | | |
|---|---|---|---|
| EP | 0 067 465 A2 | 12/1982 | |
| EP | 0 130 848 A2 | 1/1985 | |
| EP | 0 134 068 A1 | 3/1985 | |
| EP | 0 155 515 A1 | 9/1985 | |
| EP | 0 335 252 A2 | 10/1989 | |
| EP | 0 335 253 A1 | 10/1989 | |
| EP | 0 336 578 A1 | 10/1989 | |
| FR | 2 653 328 | 4/1991 | |
| GB | 2319185 A * | 5/1998 | A61F/13/15 |
| GB | 2 319 186 A | 5/1998 | |
| WO | 88/04546 | 6/1988 | |
| WO | 97/09014 | 3/1997 | |
| WO | 9822061 * | 5/1998 | A61F/13/15 |
| WO | 98/22062 | 5/1998 | |
| WO | 9925282 * | 5/1999 | A61F/13/15 |
| WO | 01/26595 | 4/2001 | |

\* cited by examiner

*Primary Examiner*—Michele Kidwell
(74) *Attorney, Agent, or Firm*—Burns, Doane, Swecker & Mathis, L.L.P.

(57) ABSTRACT

An absorbent product, such as a sanitary towel, has a stiffening element (6) which is intended to contribute to the three-dimensional shape of the product during its use. The stiffening element (6) is in a plane state before use of the product and extends in the longitudinal direction of the product over the crotch portion (3) and at least some way in over the front portion (1). The stiffening element (6) has a width (M) at the transition (12) between the crotch portion (3) and the front portion (1) which is adapted to the distance between the muscle tendons of the wearer on both sides of the crotch of the wearer in the groin of the latter and which is of the order of 15–45 mm. The stiffening element (6) extends some way in over the rear portion (2) and there consists of two separate portions (14, 15), one on each side of a longitudinal center line (L).

26 Claims, 11 Drawing Sheets

ABSORBENT ARTICLE WITH IMPROVED FIT

CROSS-REFERENCE TO RELATED APPLICATIONS

The present application claims the priority of U.S. Provisional Application No. 60/284,871, filed in the United States on Apr. 20, 2001, the entire contents of which are hereby incorporated herein by reference.

BACKGROUND OF THE INVENTION

1. Technical Field

The present invention relates to an absorbent product, such as a sanitary towel, a panty liner, an incontinence pad, a nappy or the like, which product has a longitudinal direction and a transverse direction, a front portion, a rear portion, a crotch portion located between the rear portion and the front portion, an absorbent element, a liquidtight layer, and also a stiffening element which is intended to contribute to the three-dimensional shape of the product during its use.

2. Background Art

A great many features are desired in absorbent products, such as a sanitary towel, an incontinence pad, a nappy or the like, which are not easy to accomplish simultaneously. One such feature is that the product, for example a sanitary towel, will be capable of catching and absorbing bodily fluid discharged from the wearer. Conventional sanitary towels in sizes intended for heavy flows of menstrual fluid have been of thick and relatively wide design. Sanitary towels of this type are described in, for example, U.S. Pat. No. 3,294,091. Thick and relatively wide sanitary towels of this type theoretically have great absorption capacity but in practice, when the sanitary towel is subjected to compression forces when squeezed together between the thighs of the wearer, much of the take-up capacity and absorption capacity can be lost. The sanitary towel is squeezed together into an arbitrary rope-like shape which frequently does not offer a sufficiently large receiving surface for the menstrual fluid discharged, and leakage occurs in the case of heavy flows of menstrual fluid. The sanitary towel can also be pressed together between the thighs of the wearer in such a manner that the side edges of the sanitary towel and the liquidtight layer are folded in over the liquid-permeable surface and in this way reduce the size of the liquid-receiving surface available.

Sanitary towels are intended to be positioned inside a pair of briefs, the design of which may vary. In this connection, sanitary towels can be positioned incorrectly inside the briefs. There is therefore a risk of the sanitary towel being, by mistake, positioned too far forward or too far back or displaced slightly in the lateral direction and therefore of the absorption capacity and receiving surface of the whole sanitary towel not being optimally utilized.

Conventional sanitary towels are generally retained in the briefs of the wearer by means of pressure-sensitive adhesive or friction coatings. The sanitary towel is fitted by being put in position in the briefs, after which the latter are pulled up into position. When fitting the product inside the briefs, however, it is difficult to achieve a positioning which is optimum in relation to the body of the wearer. Use is usually made of the crotch portion of the briefs in order to determine where the sanitary towel will be positioned. As sanitary towels are manufactured in a great many sizes and models, the position and design of the crotch portion provide a particularly unreliable indication of where in the briefs a sanitary towel is to be positioned, and the functioning of the sanitary towel during use is consequently not always as desired.

Another cause of leakage occurring past sanitary towels attached inside the briefs of the wearer is that the sanitary towel moves together with the briefs instead of following the body movements of the wearer. This means that even a sanitary towel which was from the outset positioned correctly in the briefs in relation to the body can be pulled out of this position by the briefs.

In order to attempt to reduce leakage arising as a result of the sanitary towel being pressed together between the legs of the wearer, it has become usual to provide the sanitary towels with special attachment flaps. It is known from, for example, SE 455 668, U.S. Pat. No. 4,285,343, EP 0 130 848, EP 0 134 086 and U.S. Pat. No. 4,608,047 to provide sanitary towels with flexible side flaps or wings projecting from the longitudinal side edges. These are intended to be folded around the edge portions of the briefs of the wearer when the sanitary towel is put on and attached to the outside of the briefs. The side flaps per se constitute protection against side edge leakage and soiling of the briefs. Moreover, deformation of the absorption body of the sanitary towel is counteracted by virtue of the fact that the sanitary towel is anchored at the leg edges of the briefs and is held extended between these during use.

However, a considerable disadvantage of providing absorbent products with such attachment flaps is that many wearers find it embarrassing that the attachment flaps are visible on the outside of the briefs. This also means that absorbent products with such attachment flaps cannot be used when, for example, the wearer is wearing a swimsuit.

Another disadvantage of the attachment flaps is that they are relatively difficult to handle and require many manual operations in order to be fitted correctly around the leg edges of the briefs. Furthermore, especially in the case of attachment flaps which extend quite a long way along the side edges of a sanitary towel, it can be virtually impossible to fold the attachment flaps around the curved leg edges of the briefs without chafing and unattractive creases in the attachment flaps occurring.

A further problem of sanitary towels with attachment flaps is that the functioning of the attachment flaps or wings depends on the design of the briefs. It goes without saying that a sanitary towel with attachment flaps interacts differently with briefs with a wide crotch compared with briefs with a very narrow crotch.

Attachment flaps or wings on sanitary towels protect the leg edges of the briefs from soiling but, as emerged above, are far from being an entirely satisfactory solution.

In order to improve leakproofness, EP 0 067 465 has proposed manufacturing a two-part sanitary towel in which the two parts are interconnected only at their end portions. The lower part is fastened in the briefs of the wearer, and the upper part makes contact with the body of the wearer. The idea is that the parts will be able to move slightly in relation to one another during use. The mobility between the parts is, however, very limited, and the known sanitary towel is still dependent on the movements of the briefs. Furthermore, there is no guarantee that the upper part will be held in contact with the body of the wearer during use.

PCT/SE96/01061 describes another two-part absorbent product in which the two parts are movable in relation to one another. This known product also has limited mobility between the parts and is to a certain extent dependent on the movements of the briefs.

One way of attempting to reduce the risk of edge leakage caused by deformation of the sanitary towel during use is to provide the sanitary towel with a preshaped raised portion, what is known as a hump, which is intended to make contact with the genitals of the wearer during use of the sanitary towel. Discharged bodily fluid can in this way be caught as soon as it leaves the body of the wearer and be absorbed immediately into the product instead of running out over the surface of the latter. A raised portion also makes it easier for the wearer to position the product correctly in relation to the body. French patent publication FR-A-2 653 328 describes a sanitary towel with a hump in the form of a central, longitudinal, cylindrical raised portion.

A common way of creating a raised portion has been quite simply to build it up by arranging a greater quantity of absorption material within the area of the raised portion. As the absorption material used is in most cases what is known as cellulose fluff pulp, however, such a raised portion collapses and loses its shape when it is wetted. In order to produce a raised portion which is sufficiently large in the wet state as well, a raised portion consisting of cellulose fluff pulp must comprise so much absorption material that it is altogether too high, hard and uncomfortable to wear in the dry state.

It is also known to produce an article with a raised portion facing the wearer by positioning a shaping element on top of the absorbent core. The disadvantage is that this interferes with the liquid transport down to the absorbent, liquid-retaining absorption core and that leakage can occur because the shaping element does not have sufficient admission capacity or temporary retention capacity. The use of, for example, a foamed material in the raised portion has been proposed. However, it has proved difficult to produce a foamed structure with sufficiently open pores for good liquid admission into the latter at the same time as the material is to have such great retention capacity that liquid is not pressed out in the event of loading originating from the wearer, for example when the latter sits down.

Another example of a raised portion is described in Swedish patent 507 798. Such a raised portion has a predictable shape, both before and during use, and also keeps its shape irrespective of the movements of the wearer and of the wetting to which it is subjected. The raised portion is anatomically designed, which means that it is relatively narrow in order to project in slightly between the labia of the wearer during use without causing discomfort for the wearer.

Although such a raised portion functions well for its purpose, it has been found that when the raised portion is exposed to large quantities of bodily fluid over a relatively short period of time, there is a risk that some of the liquid will run on the outside of the raised portion and flow out past the side edges of the absorbent product. Such leakage can occur, for example, when the wearer of a sanitary towel has been sitting or lying down for a relatively long period of time and then suddenly rises. This is because, when the wearer is sitting or lying down, a relatively large quantity of menstrual fluid accumulates in the vagina of the wearer. In the event of a sudden change in body position, the entire quantity of accumulated liquid may be discharged at once. A narrow raised portion of the type described in SE 507 798 does not then have a sufficiently large surface to be capable of receiving and absorbing the entire quantity of liquid in one go, for which reason such sudden liquid flows often result in leakage.

EP 0 335 252 and EP 0 335 253 have proposed providing an absorbent product with a deformation element. The deformation element is acted on by the transverse compressive forces between the thighs of a wearer. The purpose of the deformation element is to cause a portion of the product to bulge in the direction of the body of the wearer during use. It is difficult, however, to control or predict entirely the shape the product will adopt for each individual wearer. Moreover, it is difficult to ensure contact between the body of the wearer and the surface of the product, because the degree of bulging is determined entirely by how much the product is compressed in the transverse direction.

U.S. Pat. No. 4,804,380 describes an absorbent product which has a permanent three-dimensional shape. The product has one end portion of flat or concave shape and one end portion provided with a raised portion. The flat or concave end portion is intended to be positioned in front of the mons Veneris of the wearer, and the end portion comprising the raised portion is intended to fit between the buttocks of the wearer. The three-dimensional design of the product is brought about by folding a fairly stiff absorption body. In order to make the raised portion permanent, the rear side of the product in the end portion which is to have the raised portion is provided with a glued surface. When the raised portion has been formed, it is maintained by means of the glue.

There are absorbent products on the market which have a permanent, three-dimensional, boat-like shape and in which the outer shell consists of a moulded polymer foam.

A considerable disadvantage of permanent three-dimensional products is that it is difficult to pack a stiff three-dimensional product. Such products require a great deal of space for transport and sale, and it can be embarrassing for a wearer to carry around a sanitary towel or an incontinence pad which it is impossible to fold and therefore cannot be concealed in the hand or in the worst case will not even fit in a handbag.

EP 155 515 describes how an absorbent product, such as a sanitary towel, is imparted a bowl-shaped appearance by virtue of elastic being applied in a pretensioned state at the longitudinal side edges of the product. The use of elastic complicates manufacture, and there is a risk of the intended elastic effect being lost in connection with packing of the product or when the latter is stored in a folded packing state.

It is previously known to design plane absorbent products which adopt a three-dimensional, essentially bowl-like shape when applied. An example of this is described in U.S. Pat. No. 4,655,759. This discloses an elongate sanitary towel which consists of a layer of absorbent material, a flexible liquidtight outer layer and a liquid-permeable inner layer. The sanitary towel is provided with a pair of channels formed by stamping, the channels being located on both sides of a longitudinal center axis and extending along a curved path over the absorption material layer. The two paths together form an hourglass-like shape positioned centrally over the towel. Before use, the sanitary towels are essentially plane but, when they are applied to the wearer, they are folded into a bowl-like shape, that is to say with liquid-stopping upright borders outside the channels. A disadvantage of this bowl-like construction is that the borders hold the central portion of the sanitary towel at a distance from the genitals of the wearer, and liquid discharged from the wearer does not flow directly into the absorbent product but can run on the surface, the risk then being obvious that liquid may find an undesirable transport path in the form of a small crease or the like and run straight out of the product in the lateral or longitudinal direction. Stamped channels in an absorption body also have the disadvantage that the liquid spread in the absorption layer is disrupted and that absorption material outside the channels is not utilized, which increases the risk of local oversaturation and attendant leakage from those parts of the absorption layer which are used.

Previously known sanitary towels and the various problems associated with them have in the main been discussed above. However, what has been said above also applies to incontinence pads. Nappies for children and adults also belong to the same problem area as far as fit in the crotch and take-up of liquid in an absorption body are concerned.

As emerged above, great efforts have been made over many years in order to attempt to solve all the problems associated with absorbent products, such as sanitary towels. Although great improvements have been made, all the previously known solutions are associated with some disadvantages.

OBJECTS AND SUMMARY

By means of the present invention, an improved absorbent product of the type mentioned in the introduction has been produced. In one embodiment of the invention, the stiffening element is in a plane state before use of the product, the stiffening element extends in the longitudinal direction of the product over the crotch portion and at least some way in over the front portion, the stiffening element has a width at the transition between the crotch portion and the front portion which is adapted to the distance between the muscle tendons of the wearer on both sides of the crotch of the wearer in the groin of the latter and which is of the order of 15–45 mm, and the stiffening element also extends some way in over the rear portion and there comprises two separate portions, one on each side of a longitudinal center line.

An absorbent product according to one embodiment of the invention has a number of advantages. It is plane before use, and there are therefore no problems associated with packing, storing and transporting said product. The embodiment automatically adopts a three-dimensional bowl-like shape in an area in the front portion next to the crotch portion when the product is, at its transition between the front portion and the crotch portion, fixed in between said muscle tendons. It is known that the distance between said muscle tendons is very similar for all people. Fatness of course has an effect on the width between the thighs, but the width between the muscle groups is the same, and it is these which may cause a product to feel as if it chafes. The fat tissue lies on the outside of the muscles but does not contribute to any sensation of discomfort. The distance between said muscle tendons is the same irrespective of whether the wearer is slim, of normal weight or overweight. It has been found that what determines whether a wearer experiences discomfort in the form of pressure or chafing against the insides of the thighs is whether the absorbent product has a width during use which in the critical area considerably exceeds the distance between the muscle tendons in the groin portion. This distance has been found to be roughly 25–45 mm. It has been found that a product with a width which exceeds 40 mm in the critical area during use feels uncomfortable to wear to the majority of wearers. On the other hand, it is rarely experienced as being unpleasant if an absorbent product pushes down or aside fat tissue which may be present in the crotch area of the wearer.

Surprisingly, it has been found that this distance between said muscle tendons does not change throughout the lifetime of a person. Small infants therefore have a corresponding critical distance, which, according to the present invention, can be utilized for producing nappies with an improved fit. The same of course applies for nappies for adults. It is to be pointed out that said critical distance between the muscle tendons applies for men also, who have the same distance between said muscle tendons.

According to a preferred embodiment of the invention, the stiffening element is absorbent and at the same time constitutes the absorbent element, and it swells during absorption while on the whole retaining its geometry in the transverse direction of the product.

According to an alternative embodiment, it is possible, of course, to have a separate stiffening element behind the absorption element, seen from the side facing the wearer. However, in terms of production, it is simpler if a separate stiffening element can be eliminated. It is of course preferable from an environmental point of view also.

In the preferred embodiment, the width of the stiffening element at the transition between the crotch portion and the front portion is of the order of 30–35 mm. It has been found that a width at said transition of 30–32 mm fits well for in the order of 80% of all wearers.

According to a suitable embodiment, the side edges of the stiffening element in the front portion of the product diverge in the direction from the crotch portion at least some way in over the front portion, and in that the side edges of the stiffening element, in the direction from the crotch area, form an acute angle with a line in the longitudinal direction of the product.

An embodiment of the invention is adapted to the anatomy of the wearer. The special geometry around the transition between the crotch portion and the front portion results in a product being anchored firmly in the groins of the wearer during use, and in this way the product is prevented from moving backwards between the legs of the wearer. This is otherwise a common problem in conventional products because the leg movements of the wearer often shift the product backwards.

The stiffening element preferably has a stiffness of in the order of 1–15 N measured according to ASTM D 4032-82. This "Circular Bend Procedure" is described in detail in U.S. Pat. No. 4,950,264, the entire contents of which is hereby incorporated herein by reference.

According to a preferred embodiment of the invention, the stiffening element comprises a dry-formed fiber mat with a density between 0.15 and 0.75 $g/cm^3$ and a weight per unit area of in the order of 100–400 $g/m^2$.

In this context, the term density means the density of the fibrous material, that is to say any highly absorbent particles included in the fibrous material are not to be taken into account.

One such dry-formed fiber mat is described in U.S. Pat. No. 5,730,737. The fiber mat produced is very stiff after forming and compression. The fiber mat can be used as it is or mechanically softened to the desired stiffness.

According to a suitable embodiment of the invention, the side edges of the stiffening element, which diverge at least some way from the crotch portion in over the front portion of the product, are arranged so as to form an angle between a line in the longitudinal direction of the product and each of said side edges are in the order of 35–55°, preferably in the order of 45°. With this geometry in and around the transition between the crotch portion and the front portion, effective anchoring is obtained without the wearer experiencing any discomfort in the form of chafing or the like.

According to a preferred embodiment of the invention, the side edges of the stiffening element, in the direction from the crotch portion, diverge at least mentioned above, the crotch portion of course has a length of 80–100 mm. This length corresponds to the length of a plane portion in the crotch portion of a woman. The stiffening element according to the last embodiment is therefore anchored both at the rear and at the front at the transition between the crotch portion and the rear portion and, respectively, at the transition between the crotch portion and the front portion, as a result of which a product which is very stable, well fixed and at the same time comfortable during use is obtained.

BRIEF DESCRIPTION OF DRAWINGS

The invention will be described in greater detail below with reference to illustrative embodiments which are shown in the accompanying drawings, in which.

PREFERRED EMBODIMENTS FOR CARRYING OUT THE INVENTION

Figure 1:
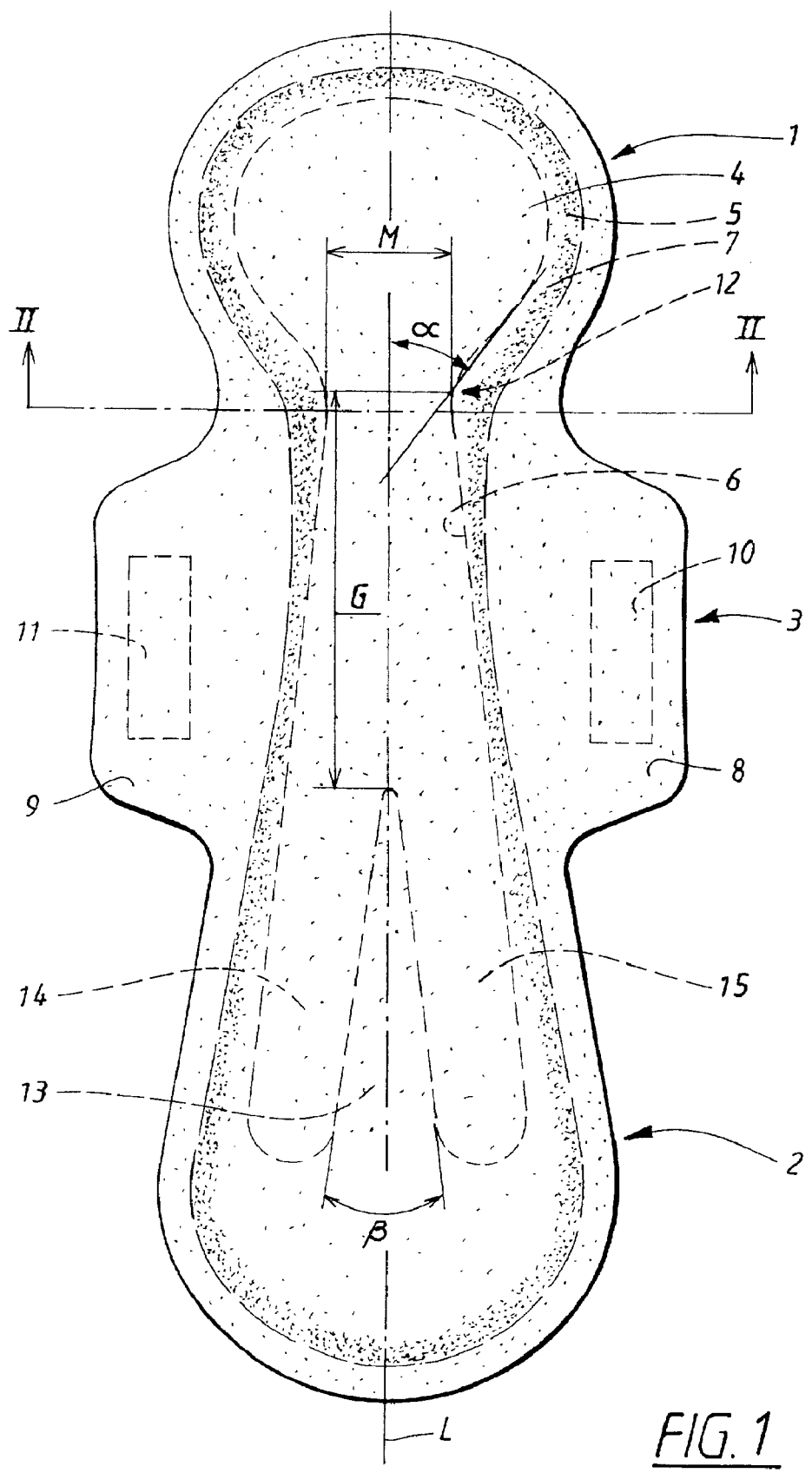
FIG. 1 shows a plan view of an absorbent product according to a first embodiment.
Figure 2:
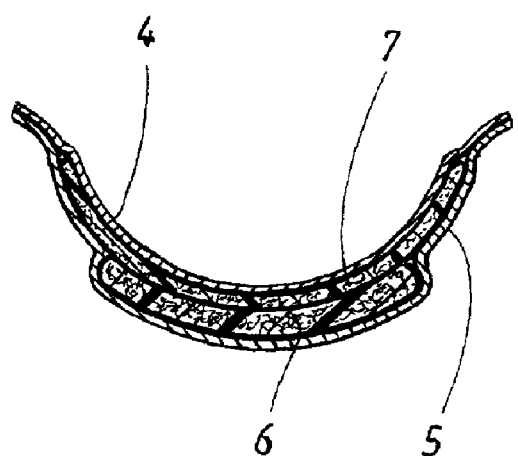
FIG. 2 shows a section along the line II—II in FIG. 1 but in a curved utilization state.

FIGS. 1 and 2 show a preferred embodiment of the invention in the form of a sanitary towel or incontinence pad. The product is elongate with a longitudinal direction and a transverse direction. The product has a front portion 1, a rear portion 2 and a crotch portion 3 located between said portions. The product shown in FIGS. 1 and 2 comprises a liquid-permeable inner layer 4 which is intended to face the wearer during use of the product. The inner layer, which makes contact directly with the skin of the wearer, is suitably made from a soft, textile-like material. Examples of suitable liquid-permeable materials are various types of what are known as non-woven fabrics. Other examples of suitable materials are perforated plastic films. Net and knitted or woven textiles and combinations and laminates of said materials can also be used as the inner layer. Examples of inner layers for sanitary towels are laminates of different non-wovens and laminates of non-wovens and perforated plastic films. The liquid-permeable layer can also be integrated with underlying drainage or absorption layers, for example a foam plastic with open pores and with a density gradient in the depth direction can serve as a surface layer and as a drainage layer and/or absorption layer.

The absorbent product also has a liquidtight outer layer 5. This usually consists of a thin plastic layer, made of polyethylene for example. It is also possible to use a liquid-permeable material which has been treated with hydrophobing agent in order to make it liquidtight. In particular if the absorbent product is relatively large, it may be suitable for the outer layer to be vapour-permeable in addition to being liquidtight. Such layers can consist of hydrophobed non-woven fabric or of porous plastic films.

The absorbent product includes an absorbent element 6 of keyhole-like shape, and a liquid-permeable insulating layer 7 which likewise has a keyhole-like shape but with a greater extent in both the longitudinal direction and the transverse direction than the absorbent element 6. The outer layer 5 and the inner layer 4 extend with edge portions outside the insulating layer around the latter and are interconnected along these edge portions to form a cover around the absorbent element 6 and the insulating layer 7. In the region of the crotch portion 3, the cover formed by the inner and outer layers extends outwards in the lateral direction to form flexible side flaps 8, 9, known as wings, which are intended to be arranged around the crotch portion on the briefs of the wearer in order to protect the edge portions of the briefs from soiling. The wings 8, 9 are suitably provided with adhesive coating, which is indicated in FIG. 1 by reference numbers 10, 11, on the outer layer 5, by means of which the wings can be attached around the legs of the briefs. As can be seen from FIG. 2, the insulating layer 7 is located directly inside the inner layer 4 and is principally intended for rapidly admitting discharged bodily fluid into the underlying absorbent element 6 and forming a liquid-insulating layer so as to reduce what is known as back-wetting from the absorbent element 6 to the inner layer 4 making contact directly with the wearer.

The insulating layer can consist of, for example, an airlaid fibrous material of low density bonded together with bonding agent or thermofiber, which is marketed under the designation LDA (low density airlaid). The absorbent element 6 is, seen from the liquid-permeable inner layer 4, arranged under the insulating layer 7. In the preferred embodiment, this element is designed to take up and retain essentially all the bodily fluid discharged. The absorbent element 6 has smaller capillaries than the insulating layer 7 located above and therefore draws liquid from the insulating layer and reduces back-wetting by liquid from the absorbent element to the insulating element and to the inner layer 4 which remains essentially dry during use of the product. Only when the absorbent element is saturated with liquid can transport take place from the absorbent element to the insulating layer.

In the illustrative embodiment shown, the absorbent element 6 is also intended to serve as a stiffening element and is for this purpose designed so as to be very stiff in order, as far as possible, to avoid the absorbent product being compressed in an uncontrolled manner in the event of squeezing forces in the lateral direction generated by the thighs of the wearer in the crotch area. The absorbent stiffening element has a size, shape and stiffness which result in the product, throughout its time of use, retaining a predetermined shape and moreover being retained in the intended position on the wearer. As can be seen from FIG. 1, the absorbent stiffening element 6 extends over the front portion, the entire crotch portion 3 and a considerable part of the rear portion 2.

At the transition 12 between the crotch portion 3 and the front portion 1, the stiffening element 6 has a width M which is adapted to the distance between two particular muscle tendons on both sides of the crotch of the wearer directly in front of the groins. These muscle tendons form part of the muscle group which originates on the inside of the pelvic diaphragm and has its attachment along the thigh. This muscle group consists of the adductor brevis, adductor longus, gracilis and adductor magnus muscles. As mentioned above, it is known that this distance between said muscle tendons is very similar for all people. This dimension is in the order of 25–45 mm. Research has shown that 80% of all women have a dimension of 30–32 mm between said muscle tendons. When said width M essentially corresponds to the distance between said muscle tendons on the wearer, the product will during use be anchored firmly with the transition portion between the muscle tendons and be retained in this position. The two side edges of the front portion diverge in the forward direction on the product from said transition area 12. In this way, the product is substantially prevented from moving backwards between the legs of the wearer. This is a common problem in conventional sanitary towels because the leg movements of the wearer often shift the sanitary towel backwards.

In FIG. 1, an angle between a line in the longitudinal direction of the product and each of said side edges has been designated by $\alpha$. In the case of a large angle $\alpha$, for example close to 90°, the edges of the front portion may chafe against the groins and legs of the wearer and in this way cause discomfort for the wearer. The smaller the angle $\alpha$, the greater the risk that the product will slide backwards in between the legs of the wearer. In the case of an angle of less than 30°, this risk is high. An angle of 35–45° provides the best balance between secure positioning and comfort. An angle of 45° has been found to be especially favourable.

An exemplary absorbent product, such as a sanitary towel, according to one embodiment of the invention is designed with a crotch length adapted to the anatomy of the wearer. In one embodiment of a sanitary towel according to the invention, use has been made of the fact that the great majority of women have a crotch length of in the order of 80–100 mm. The stiffening element 6 in the preferred embodiment has therefore been designed with a corresponding crotch length G of in the order of 70–120 mm, that is to say, the distance from the transition area 12 to the start of the rear portion. Along the crotch, where the body shape of the wearer is essentially plane, the sanitary towel according to the invention is designed so as in the dry state to be relatively stiff in the lateral direction, that is to say it is sufficiently stiff not to be deformed in the lateral direction and form creases. As the stiffening element 6 in the embodiment described here also constitutes the major part of the absorption capacity of the sanitary towel, it is preferable to be capable of utilizing available space between the legs of the wearer in the crotch. The width of the sanitary towel in the crotch area is, with regard to the stiffening element, limited at the front by said distance between said muscle tendons directly in front of the groins of the wearer. In the backward direction from said transition area to the end of the crotch portion, the width of the stiffening element 6 and thus the absorbent element can increase continuously to in the order of 1.5 times the width in the transition area 12 between the crotch portion and the front portion without any risk of the stiffening element chafing the wearer in the crotch.

The abovementioned geometrical design of the area in and around the transition area 12, that is to say the size of the angle $\alpha$ and the width M, and also the selected crotch length G on the stiffening element for the product according to a preferred embodiment of the invention, affords a very good anatomical adaptation of the stiffening element, which gives the product a good fit and stability of the product in the fitted position on the wearer. This is of particularly great importance for the functioning of the product, not least because the wetting point can, on account of the body position of the genitals of the wearer in the longitudinal direction of the crotch area, vary by as much as in the order of 20 mm for different wearers. As the available space around the wetting point is very limited in width and length, optimum positioning and anchoring in this position of the stiffening absorbent element is preferable. This is achieved by means of said distances M and G selected and said angle $\alpha$ selected.

The anchoring effect may be achieved at said muscle tendons even when the width M on the product is less than the distance between said muscle tendons directly in front of the groins. The two edge portions of the front portion diverge in the forward direction, and the product can slide backwards slightly until the edge portions are anchored firmly between said muscle tendons. The distance M on the embodiment is suitably of the order of 15–35 mm, and preferably 25–30 mm. The latter distance fits most wearers. If the distance exceeds roughly 35 mm, the product may feel uncomfortable to some wearers. A distance in excess of 45 mm may be undesirable because such products may cause discomfort in the form of chafing for most wearers.

The stiffening element 6 and therefore the absorption element also extend some way in over the rear portion 2 of the product. In the rear portion of a preferred embodiment, the stiffening element has a cutout 13 extending from the end edge of the stiffening element in the direction of the crotch portion, as a result of which the product can fold along a longitudinal line in the cutout and the parts, the legs 14 and 15, which are located on both sides of the cutout are more flexible than the wider crotch portion and can be made vertically movable in relation to one another by selecting the width of the cutout accordingly. This cutout 13 aids in the adaptation and flexibility of the product in relation to the body. The fold in the cutout can penetrate the cleft between the buttocks of the wearer and in this way provides very good protection against leakage via the cleft between the buttocks, which type of leakage usually occurs during the use of conventional products when the wearer is lying on her back. The cutout 13 also makes it possible for said legs 14, 15 on the stiffening element to be displaced vertically in relation to one another during different body movements, for example when the wearer is walking.

In the illustrative embodiment shown in FIG. 1, the cutout 13 is wedge-shaped and located symmetrically in relation to the longitudinal symmetry line L of the product and also forms an angle $\beta$ in the order of 20°. This angle can vary within wide limits but of course depends on the design of the rear portion 2. In the case of a considerably wider design of the rear portion, such as in the design according to FIG. 5, said angle $\beta$ can vary between 10° and 120°, preferably between 15° and 40°.

The stiffening element 6 also serves as the main absorption element of the product and has very great liquid-spreading capacity for rapid spreading of bodily fluid received from the wearer in the narrow crotch area directly in front of the genitals of the wearer over the absorbent portions of the whole product, that is to say over the entire stiffening and at the same time liquid-absorbing element 6. This stiffening absorbent element of the preferred embodiment is designed so as to swell in the depth direction during absorption and on the whole retain its geometry in the transverse direction of the product, which results in the stiffening element retaining its fit and secure positioning in relation to the body of the wearer throughout use of the product. The absorbent stiffening element 6 has great swelling capacity in the depth direction and attendant great absorption capacity.

According to a suitable embodiment, the stiffening absorbent element 6 consists of a dry-formed fiber mat with a density between 0.15 and 0.75 g/cm$^3$ and a weight per unit area of in the order of 100–400 g/m$^2$. An exemplary dry-formed fiber mat is described in U.S. Pat. No. 5,730,737. The fiber mat produced is very stiff after forming and compression. The fiber mat can be used as it is or mechanically softened to the desired stiffness.

The selection of compression pattern also makes it possible to vary the extensibility of the fiber mat. The dry-formed fiber mat can be made with the desired reduced stiffness and the desired extensibility by virtue of the degree of compression selected and the compression pattern selected.

Furthermore, in one embodiment, it is possible to pattern-compress only specific zones for the purpose of imparting to only these zones an extensibility and stiffness which are different from the rest of the stiffening absorption element. In another embodiment, the stiffening absorption element can be compressed over its entire extent but with different patterns in different zones. By means of the presence of a stiffening absorption element which can in a simple manner, by virtue of the pattern compression selected, be imparted the desired stiffness and the desired extension in different zones, and in which the stiffness and extension properties can be selected essentially freely in these zones, the controlling and guiding the shaping of an absorbent product intended for taking up bodily fluids can be accomplished in a new and previously unknown way.

As mentioned above, the stiffening absorbent element 6 has great swelling capacity in the depth direction, which, when a dry-formed fiber mat as above is used, has been achieved by great compression of the fiber mat in conjunction with its production. In the dry state, the fiber mat is hard-compressed and stiff, which affords the shaped and anatomically adapted absorption element very good stability in the fitted position on the wearer and very great spreading capacity, as a result of which the total absorption capacity of the absorption element can be optimally utilized and leakage caused by local oversaturation can to a great extent be eliminated. During absorption of liquid, the absorption body swells mainly in the depth direction but the absorption element does of course swell slightly in other directions as well. When the anatomically adapted stiffening absorption element swells, further improved anatomical adaptation is in fact achieved, which contributes to the stability and flexibility of the product in relation to the body shape of the wearer when the stiffness of the absorption element decreases during absorption and attendant swelling.

So as to function in the desired manner, the stiffening element preferably has a stiffness of in the order of 1–15 N measured according to ASTM D 4032-82. This "Circular Bend Procedure" is described in detail in EP 336 578.

The stiffening absorbent element can also consist of a laminate of a number of non-woven fabric layers or tissue layers which are mutually fixed for increased stiffness and which have highly absorbent particles between the individual layers. The individual layers can be fixed to one another by a bonding agent, such as adhesive or melt fibers. The highly absorbent particles can also contribute to bonding. The stiffness is controlled by means of the selection of the number of layers and quantity of bonding agent included and the selection of highly absorbent material and how the adhesive capacity thereof is utilized.

A stiffening absorbent element of this type can also be imparted different stiffness and different extensibility in different zones of the extent of the element. These properties can in this case as well be controlled by means of the compression pattern. This compression can be combined with the supply of heat, which supply can vary in different zones. Furthermore, bonding agent can be applied in different patterns to control the shaping of the stiffening absorption element during use. A varying supply of moisture in different areas is another parameter for controlling the shaping of the product during use.

Another example of the construction of a unit serving as both absorption element and stiffening element is a number of layers of LDA, that is to say layers of the same type as in the draining and insulating layer 7. However, the layers of LDA in the stiffening absorption element are bonded much more firmly both within and between the individual layers. This bonding is suitably brought about by using both melt fibers and latex, what is known as the multibond technique. In this design as well, stiffness and extensibility can be controlled by means of the selection of compression pattern and by variation of the heat supply in different zones.

Pattern compression can be used in all the material examples described above, and it is then possible to achieve, for example, hinge effects along compression lines or compression zones.

Pattern formation can take place in conjunction with compression of the stiffening absorption element. Alternatively, pattern compression can take place in a separate step after smooth compression. Use can be made of, for example, a web of a smooth-compressed material made in one of the ways described above as the starting material for the stiffening absorption element, which is pattern-compressed in the desired manner and depending on the type and size of product to be manufactured. After pattern-compression, individual products are cut out. Pattern-compression and cutting-out of separate stiffening absorption elements can take place in a single step in a combined cutting and pattern-compression unit.

As described above, the stiffening element can also constitute the main absorption element of the product. This is particularly suitable from the point of view of production because there are fewer elements to handle than if, for example, the stiffening element and the absorption element constitute separate elements.

The invention also comprises designs in which the stiffening element is separate from the main absorption element of the product. The stiffening element can then be absorbent or non-absorbent. The main purpose is to constitute a stiffening shaping element.

In addition to the interpretation of the term stiffening element as constituting a completely separate element or constituting both the main absorption element and the stiffening element of the product, the term can also embrace the interpretation that all the material plies, bonding agents etc. included in the product in the area of the desired stiffening together form the desired stiffening element. For example, a unit serving as a stiffening element and at the same time as an absorption element, with the M and G dimensions indicated above and with the geometry described above but with stiffness which is per se inadequate, is included in the invention if the necessary stiffness is obtained by being bonded together with other material plies in the area of the stiffening element.

Figure 3:
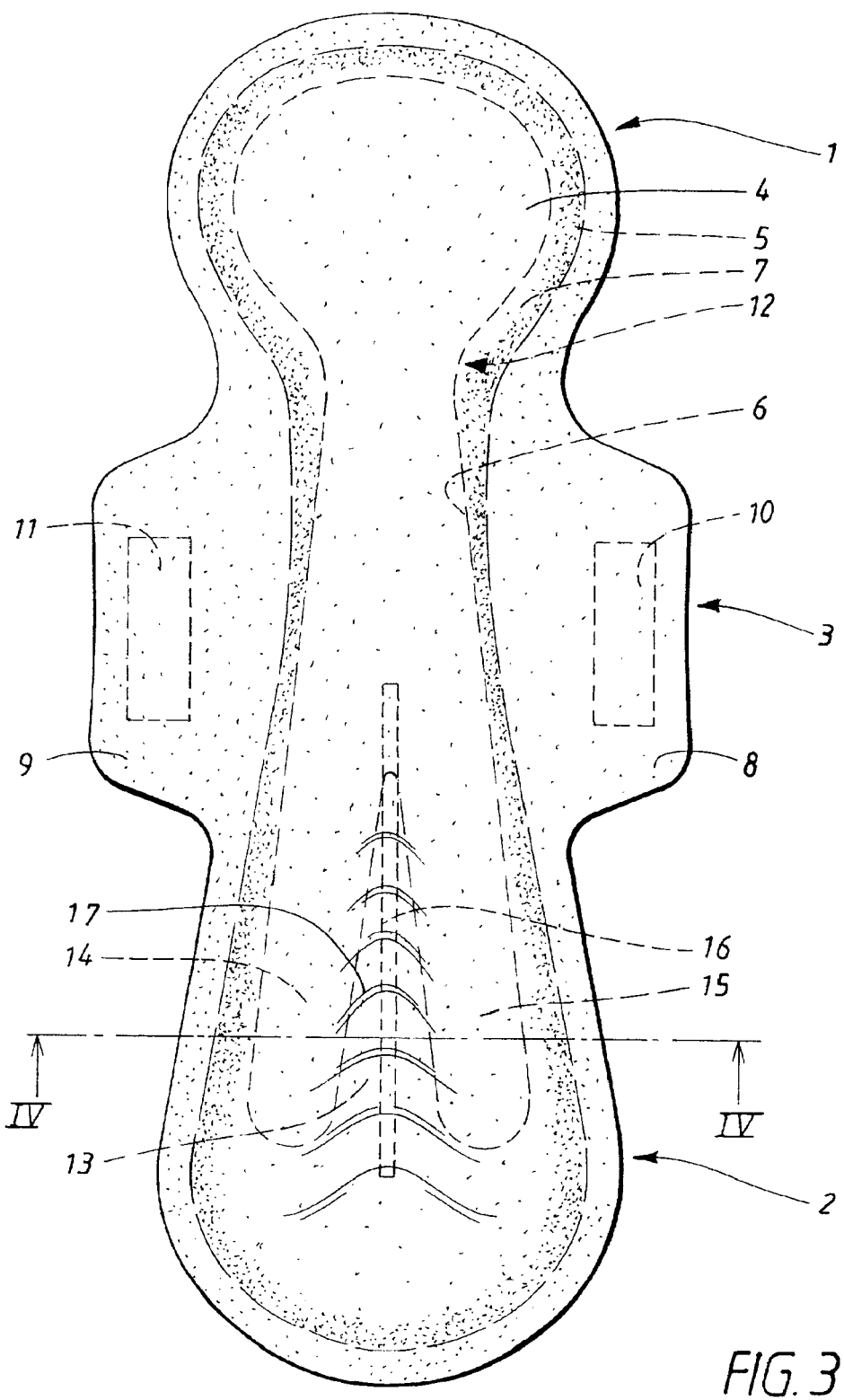
FIG. 3 shows an embodiment, slightly modified in relation to the embodiment according to FIG. 1, of a product according to the invention in a plan view.
Figure 4:
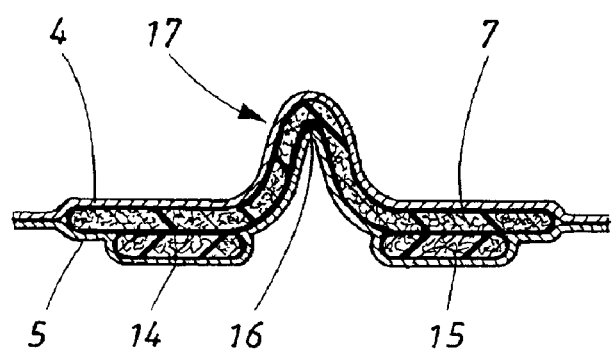
FIG. 4 shows a section along the line IV—IV in FIG. 3.

The embodiment shown in FIG. 3 differs from the embodiment shown in FIGS. 1 and 2 only in that an elastic means 16 is arranged in a pretensioned state in the longitudinal direction of the product and centrally along the rear portion 2 of the product. The same reference numbers have been used in FIGS. 3 and 4 as in the embodiment according to FIGS. 1 and 2.

The elastic means 16 is arranged centrally in the cutout and extends in the rear portion slightly beyond the ends of the legs 14 and 15 and in the other direction some way in over the crotch portion. The elastic means is arranged on the inside or on the outside of the liquidtight outer layer and is connected to the latter and/or other layers forming part of the product. The extent of the elastic means is not critical but can vary somewhat in relation to the illustrative embodiment shown in FIG. 3. The purpose of the elastic means 16 is, during use of the product, to draw adjacent material portions together and curve the product in the upward direction towards the body of the wearer for better contact with the body. The purpose is also to initiate and form the fold 17 which, during use of the product, is intended to penetrate a little way into the cleft between the buttocks of the wearer and prevent leakage of bodily fluid backwards along the cleft between the buttocks, which leakage can otherwise occur when the wearer is lying on her back.

Figure 5:
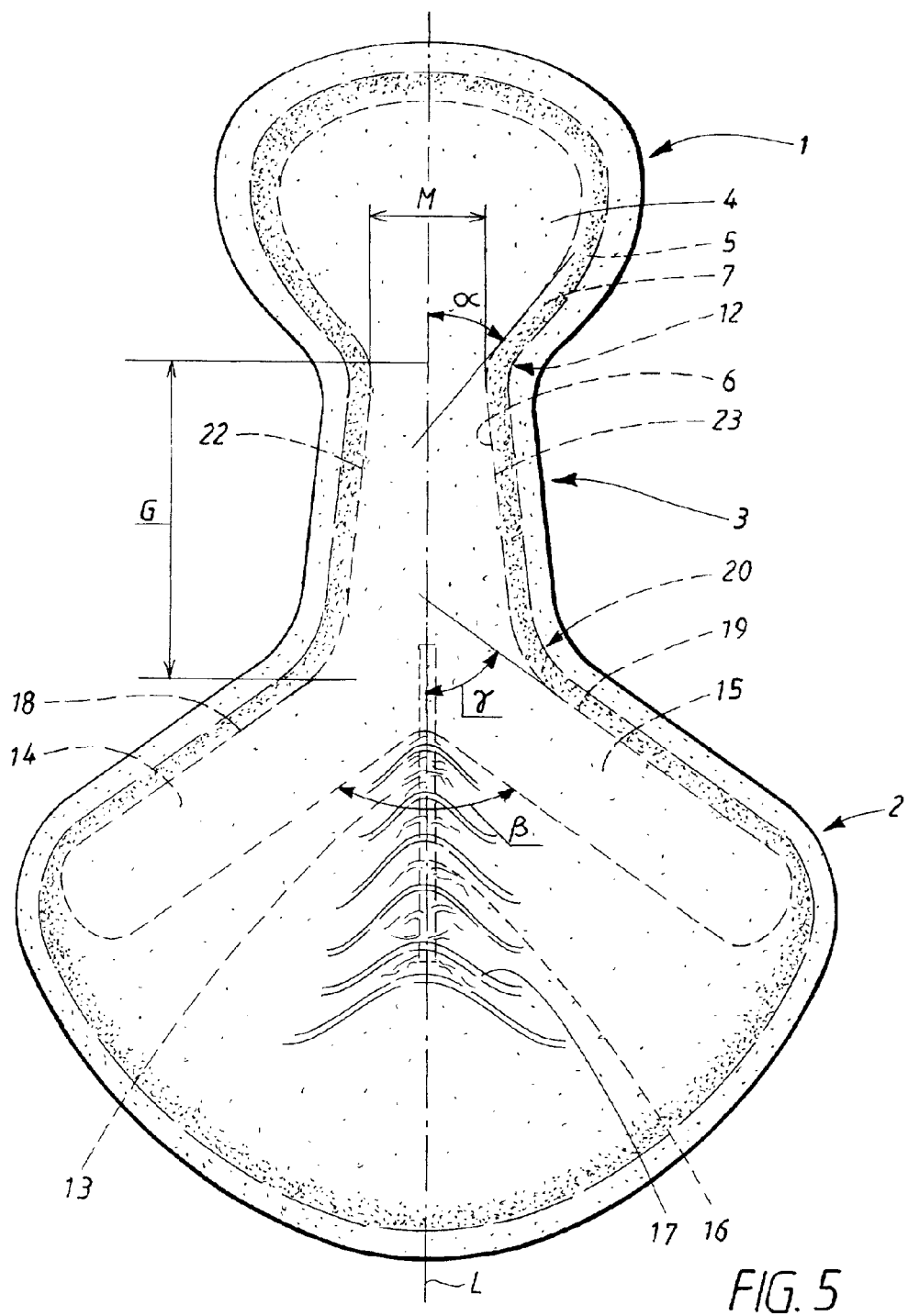
FIG. 5 shows a plan view of a third embodiment of the invention.

In the embodiment shown in FIG. 5, the components which correspond to similar parts in the embodiments according to FIGS. 1–4 have been provided with the same reference numbers. The product in the embodiment according to FIG. 5 is provided with a considerably wider rear portion 2. The product also differs from the embodiments described above in that there are no wings for attachment around the crotch portion of the briefs of the wearer.

The stiffening element 6 extends with its leg portions 14, 15 in over the rear portion 2. The outer side edges 18, 19 on the legs 14, 15 of the stiffening element 6 diverge from the crotch portion in over the rear portion. In a rear transition area 20 between the crotch portion 3 and the rear portion 2, said outer edge sides 18, 19 abruptly change direction in relation to the edge sides 22, 23 on the stiffening element in the crotch portion of the product.

The purpose of the edge sides 18, 19 of the stiffening element diverging in the backward direction on the rear portion 2 is that the product, in addition to being anchored firmly at the transition 12 between the front portion and the crotch portion, will also be anchored at the rear in the transition area between the crotch portion 3 and the rear portion 2, as a result of which the product is very stable and well fixed on the wearer during use at the same time as it feels comfortable for the wearer by virtue of its anatomical adaptation in terms of shape, size and geometry. In the drawing, an angle between the longitudinal direction of the product and each outer edge side 18, 19 has been designated γ. For a good anchoring function, this angle should preferably not be less than roughly 30°. Furthermore, so as not to feel uncomfortable, the angle should preferably not exceed roughly 60°.

The distance G between the transition areas 12 and 20 is adapted to the crotch length of a wearer and, as mentioned above in connection with the embodiments according to FIGS. 1–4, this distance G is suitably in the order of 70–120 mm. As mentioned above, the essentially plane area of the crotch of women directly in front of the genitals has a length of in the order of 80–100 mm, that is to say all women are essentially the same size in this plane area. It has been found that a crotch dimension G on the product of in the order of 70–120 mm functions well for most wearers. The larger the angles α and γ and the stiffer the stiffening element, the more important it is that the crotch dimension on the product corresponds to the length of the plane crotch portion of the intended wearer directly in front of her genitals if the product is not to feel uncomfortable.

It may therefore be suitable to have a range of sizes of the product according to the invention depending on the selection of stiffness and said angles, so that different wearers can find a suitable size with regard to dimensions and angles. This of course applies to all the embodiments of the invention described here but is particularly important when the product is intended to be anchored both at the front and at the rear. The requirement for size adaptation also increases for all the embodiments the stiffer the absorbent element is.

The stiffening element and at the same time the absorption element 6 in the embodiment according to FIG. 5 has a cutout 13. As in the other illustrative embodiments described above, this is wedge-shaped but has a larger angle β which in FIG. 5 is obtuse. The angle β can be varied within wide limits between 10° and 120°. How large a cutout 13 is required depends on the function required of the legs 14 and 15 and on the absorption capacity desired in the rear portion 2 of the product.

The smaller the angle β with the same width on the rear portion as a whole and with the same angle γ, the wider the legs 14, 15 are, which in turn results in increased absorption capacity and increased stiffness in the rear portion.

The size of the cutout also affects the height of the fold 17. This height of the fold and the shaping of the rear piece 2 also depend on the pretensioning and extent of the elastic means 16.

The illustrative embodiment shown in FIG. 5 can serve as, for example, a night towel. Like the other embodiments, this embodiment is also suitable as an incontinence pad. This type of protection is to be capable of dealing with rapidly receiving large quantities of liquid discharged at a great flow rate from the wearer.

A product of the type shown in FIG. 5 can, in combination with supporting briefs or with elastic pants adapted specially for supporting the product, serve as a nappy for receiving both urine and faeces. If the product is to serve as a nappy, the cutout 13 should be relatively large, corresponding on the whole to the embodiment shown in FIG. 5, in order that it will be possible for discharged faeces to be taken up in the cutout 13 of the rear portion.

Figure 6:
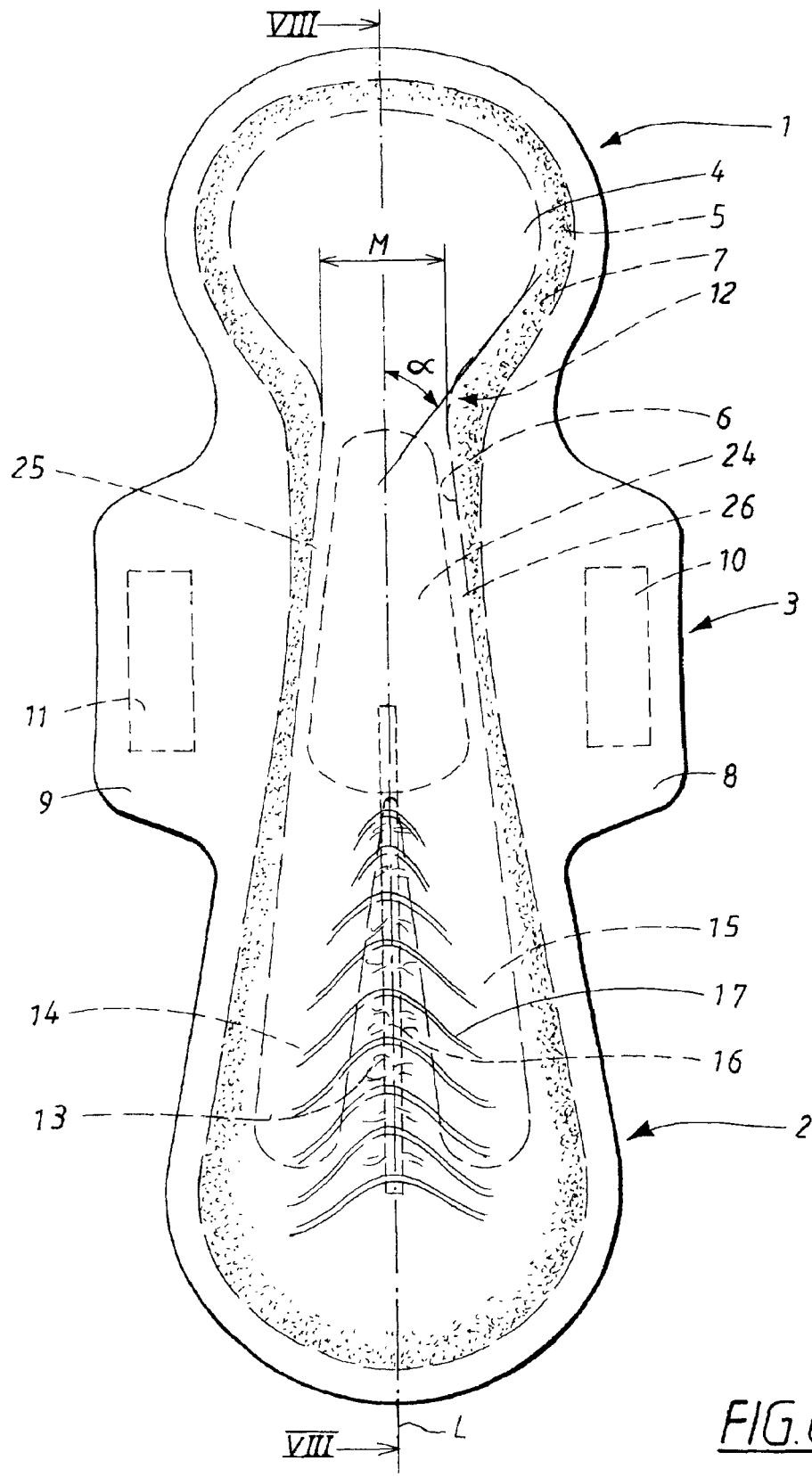
FIG. 6 shows a plan view of a fourth embodiment of the invention seen towards that surface of the product which receives bodily fluids.
Figure 7:
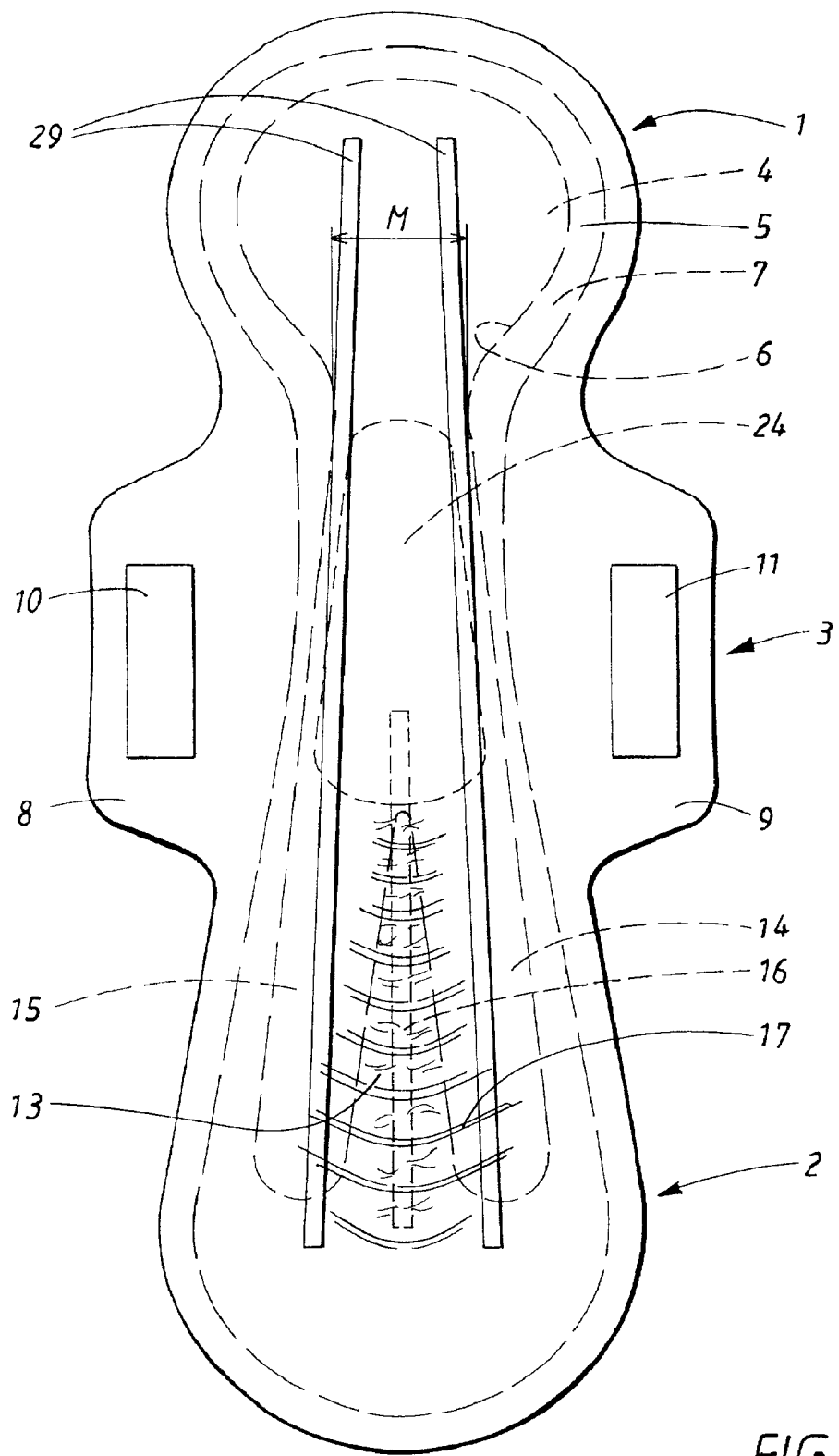
FIG. 7 shows a plan view of the product according to FIG. 6 from the opposite side.
Figure 8:
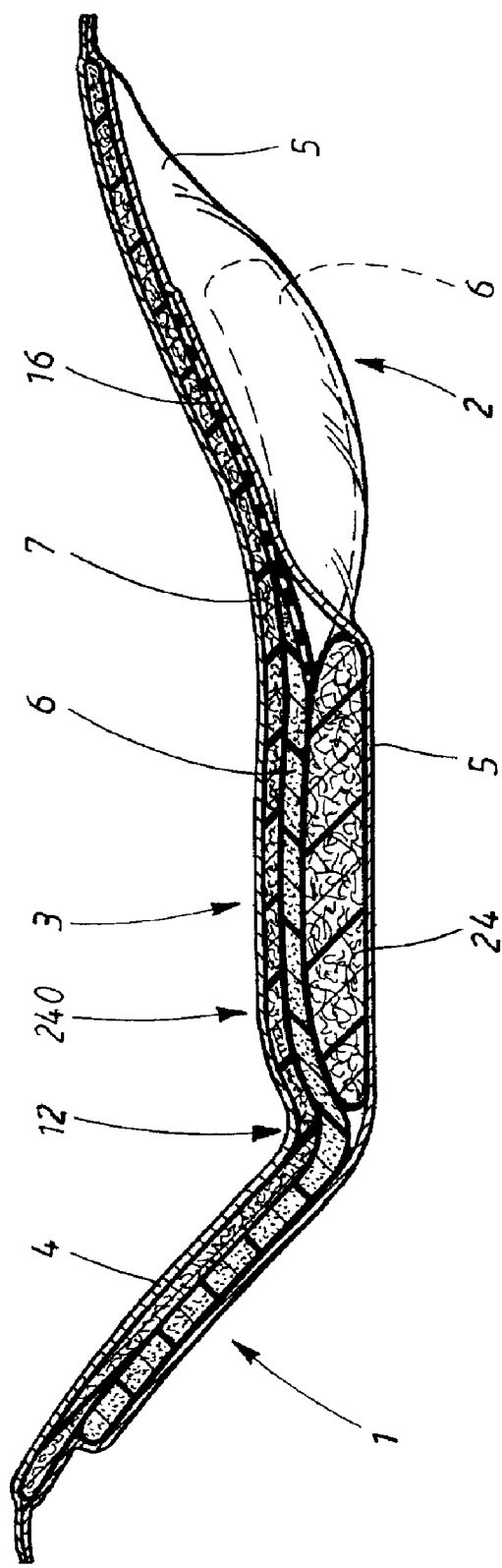
FIG. 8 shows a section along the line VIII—VIII in FIG. 6 but in a curved utilization state.

FIGS. 6–8 show another embodiment of the invention. This embodiment corresponds in many respects to the embodiments according to FIGS. 1–4, and those parts corresponding to the same parts in the embodiments described above have been provided with the same reference numbers in the drawing.

A way of reducing further the risk of edge leakage caused by the sanitary towel being deformed during use, in addition to the arrangement of the stiffening element 6, is to provide the sanitary towel with a raised portion, what is known as a hump, which is intended to make contact with the genitals of the wearer during use of the sanitary towel. Discharged bodily fluid can in this way be caught as soon as it leaves the body of the wearer and be absorbed immediately into the product instead of running out over the surface of the latter.

In the embodiment shown in FIGS. 6–8, the hump is brought about by a hump-forming element 24 which, as can be seen most clearly from FIG. 8, is arranged below the stiffening element 6 inside the liquid-impermeable outer layer 5. The positioning of the hump-forming element results in a number of advantages. Admission of bodily fluid is not interfered with by hump material in direct proximity to the genitals of the wearer, but the parts located closest to the genitals of the wearer can be optimized with regard to admission and absorption capacity. The positioning selected for the hump-forming element below the stiffening element 6 in combination with the positioning along the crotch portion of the product also results in the positive effect that the product curves and shapes itself in the desired manner when fitted on the wearer. At the transition 12 between the crotch portion 3 and the front portion, a point of inflexion is formed, in front of which, that is to say in the front portion of the product, the product is concave at least over a portion closest to said transition 12. Behind said point of inflexion, that is to say along the crotch portion of the product, the product is, in the area directly in front of the hump-forming element, convex, that is to say the stiffening element 6 is curved in this area, upwards in the crotch portion 3, as can be seen most clearly from FIG. 8. In addition to bringing about the raised portion on the front side of the product, the hump-forming element makes it possible to guide the stiffening element in the desired direction of curvature at different points of the extent of the stiffening element.

The hump-forming element 24 consists of, for example, a non-absorbent synthetic wadding which has resilient properties. Such a hump-forming element retains its shape and function even when the material is in a wet state.

The hump-forming element can also consist of a foamed material, for example polyurethane foam.

As the hump-forming material is, in the embodiment shown, located below the absorbent element, which also serves as the stiffening element, the hump-forming material can be liquid-absorbing. In such an embodiment, it is suitable to select a material which has larger capillaries than the absorption element has, so that liquid can be transported to the hump-forming material only when the absorption element is saturated with liquid. A hump-forming absorbent fibrous layer which has resilient properties only in the dry state can therefore also be used in such a construction because the material is essentially dry until the absorption element itself is saturated with liquid. The positioning of the hump-forming element 24 below both the stiffening and the absorbent element therefore affords a number of important advantages.

The element forming the raised portion has an elongate shape and extends over the entire crotch portion in the illustrative embodiment shown. The length of the raised portion can vary between roughly 20 mm and 120 mm.

The element 24 forming the raised portion is narrower than the product as a whole in the crotch area. In this way, it is possible for laterally surrounding portions 25, 26 of the product as a whole to shape themselves around the element 24 forming the raised portion. The material forming the raised portion is suitably at least twice as thick as the surrounding areas 25, 26.

In FIG. 8, the product has been shown in curved, three-dimensional form for the sake of clarity. An absorbent product of the type described here is of course always three-dimensional in the conventional sense, that is to say it has length, width and thickness.

In this context, however, the term three-dimensional means that the product is curved in some way to adapt to the body shape of the wearer.

In this context, the term plane form means that the product is essentially planar. The product shown in FIGS. 6 and 7 is essentially planiform according to this definition in spite of the fact that the elastic means draws the material layers together in the cutout 13 between the legs 14, 15.

Products in plane form according to FIGS. 6 and 7 can be packed simply, for example in stacks in a box or bag and yet, when put on, be made to adopt an anatomically adapted three-dimensional shape, as shown in FIG. 8, without any measures whatsoever.

By virtue of its special construction with the dimension of the distance M between said muscle tendons, the hump-shaped element 24, the action of the elastic means 16 and the stiffness and geometric shape of the stiffening element 6, the product is anatomically adapted and predestined to adopt during handling a three-dimensional shape according to FIG. 8 adapted to the body shape of the wearer.

Figure 9:
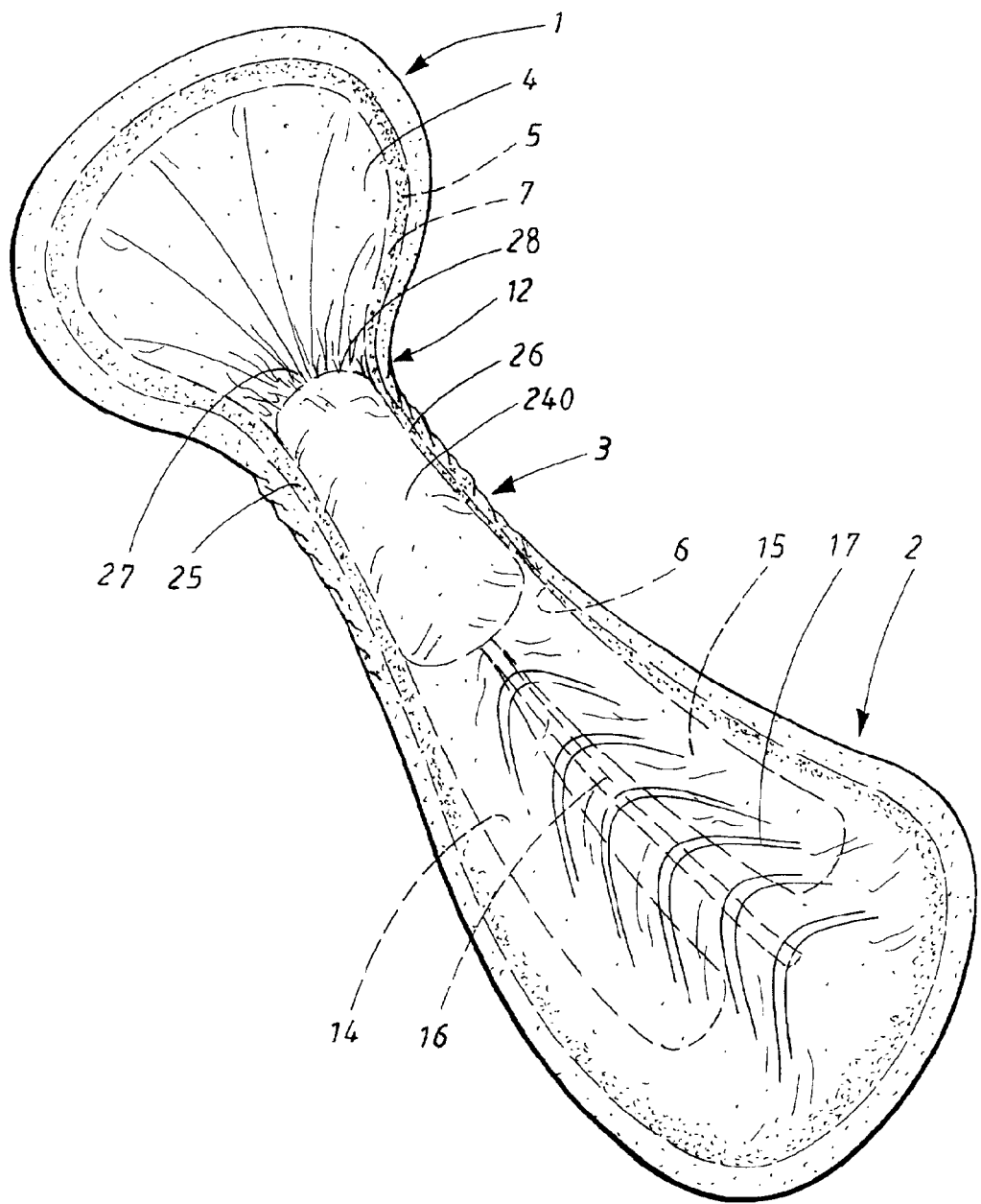
FIG. 9 shows the product according to the fourth embodiment, also shown in FIGS. 6–8, in perspective and in a utilization state.
Figure 10:
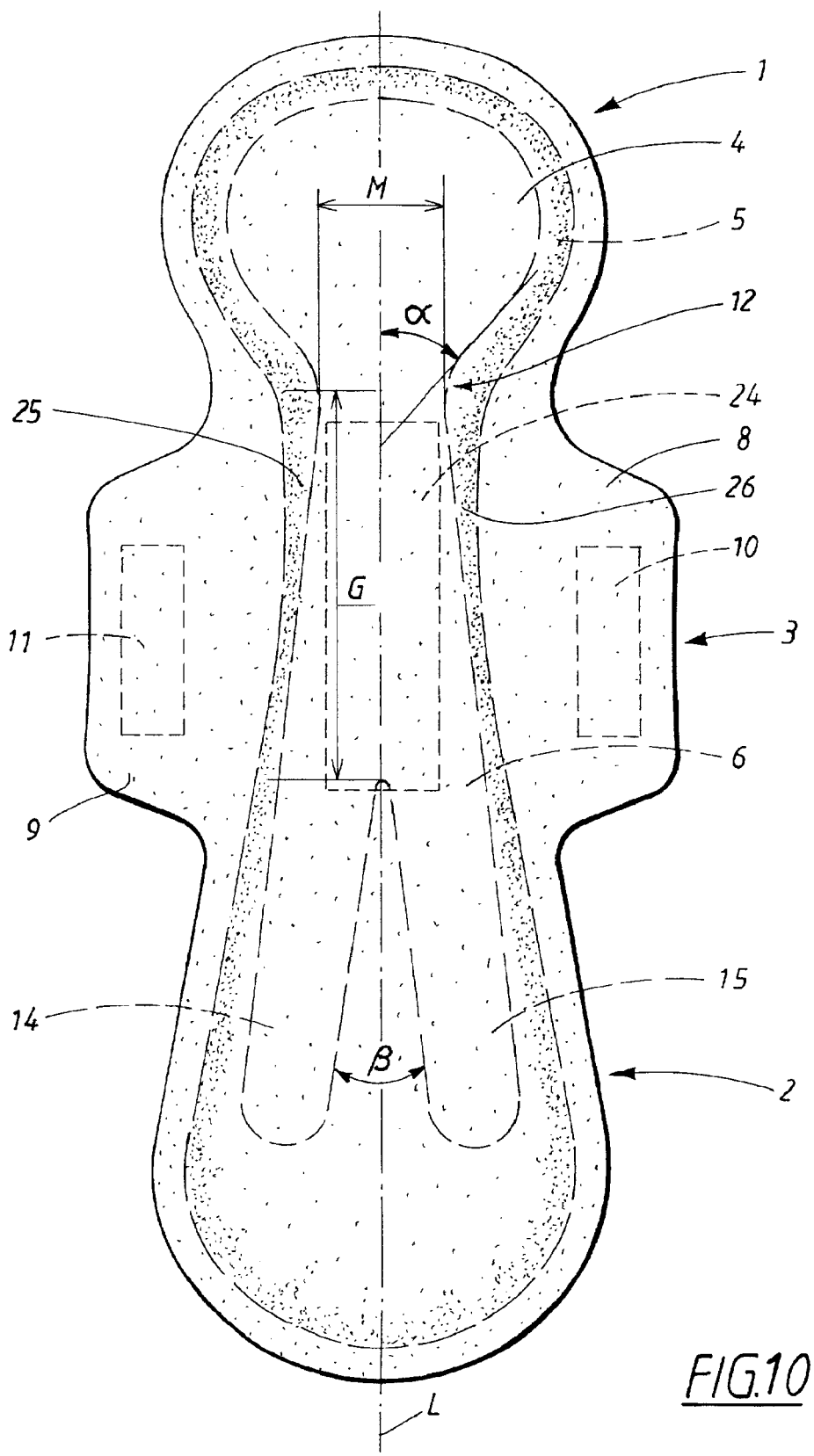
FIG. 10 shows a plan view of a fifth embodiment, slightly simplified in relation to the embodiment according to FIGS. 6–9.

In the illustrative embodiment shown, the stiffening and at the same time absorbent element 6 has the same stiffness properties over its entire extent. As a result, uncontrolled creases, which could give rise to uncontrolled and unintentional liquid flow, do not normally arise over the extent of the stiffening element. At the transition 12 between the crotch portion 3 and the front portion 1, a curvature is initiated because the product as a whole changes its flexural resistance here, on the one hand on account of the hump-forming element having its end directly in front of this transition and on the other hand because the stiffening element is at its narrowest here with a dimension M adapted to the distance between said muscle tendons on the wearer. At this transition 12, a point of inflexion 27, or rather a line of inflexion, is formed, in front of which the product is concave and bowl-shaped, whereas it adopts a convex shape behind this point of inflexion 27. As can be seen from FIG. 9, it is suitable for the hump-forming element to be rounded at the front along a line 28. In this way, the stiffening element is caused by this rounded line to adopt an evenly rounded bowl shape in the front portion, as can be seen from FIG. 9.

In the transition area 20 between the crotch portion 3 and the rear portion as well, it is suitable for the hump-forming element 24, which in the embodiment shown extends as far as said transition area 20, to be rounded at its rear end. As a result, no undesirable creases arise, but the transition between the convex crotch portion and the two side portions of the rear portion 2 sloping downwards around the fold 17 formed by the elastic means 16 is even and smooth without undesirable creases.

The raised portion formed by the hump-forming element 24 also has the advantage that the fold extending into the cleft between the buttocks of the wearer does not extend in too abruptly or too far and give rise to chafing. In this respect also, the hump provides a soft transition in the transition area between the crotch portion and the rear portion.

In all the embodiments described above, it is suitable, although not necessary, for the product to be provided with a pressure-sensitive adhesive on the outside of its liquid-impermeable outer layer 5. This has been indicated in FIG. 7 by adhesive strands 29 which, before use of the product, are covered in a conventional manner by a cover strip (not shown) treated with release agent. Although the product according to the invention is anatomically adapted, it is suitable, for reliable secure positioning, to have a pressure-sensitive adhesive on the liquid-impermeable outside of the product for interaction with the briefs of the wearer, which contributes to keeping the product in the intended position on the wearer.

Figure 11:
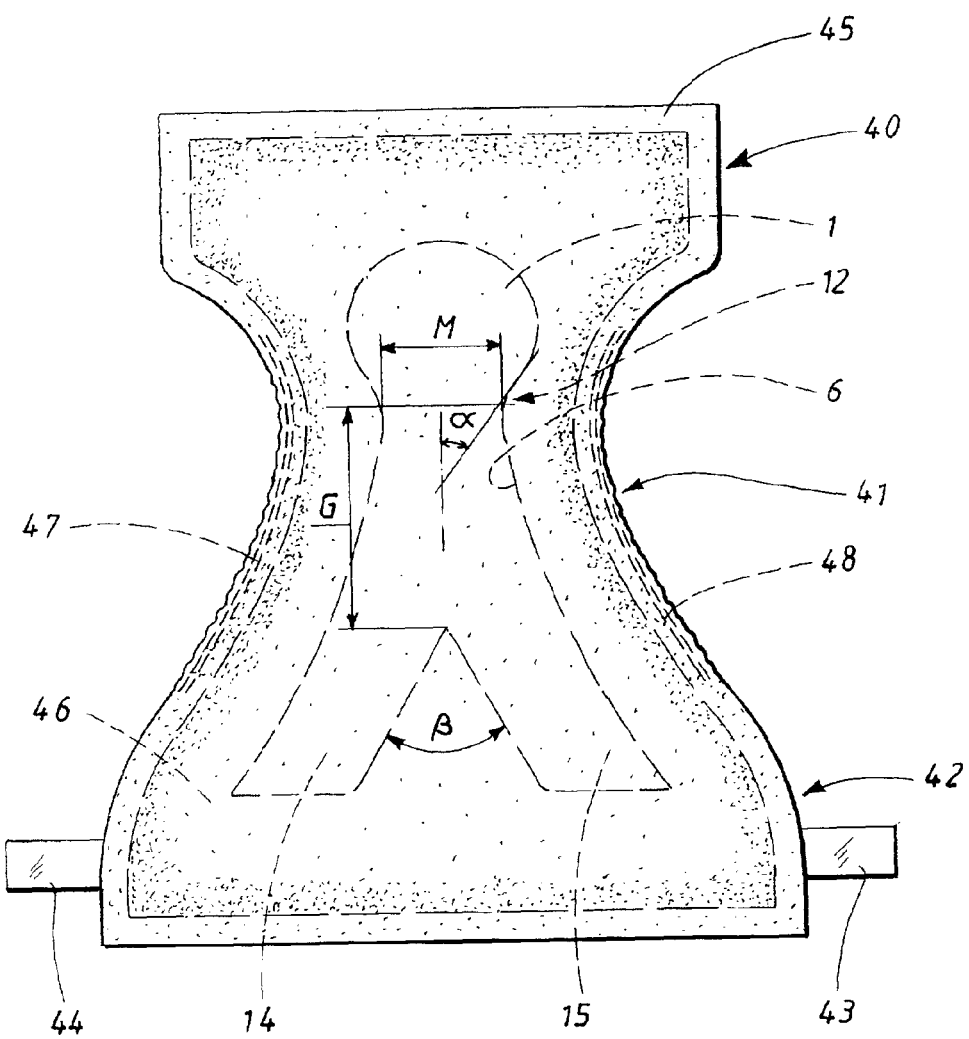
FIG. 11 shows a plan view of an absorbent product according to the invention in the form of a nappy.

FIG. 11 shows an embodiment in the form of a nappy. This has a front portion 40, a crotch portion 41 and a rear portion 42. The front portion 40 and the rear portion 42 are intended to be arranged around the waist of the wearer when the nappy is put on and to be closed in the fitted position by means of tape flaps 43, 44. In FIG. 11, the nappy is shown diagrammatically in plane form from the inside and is provided with a covering in the form of a liquid-permeable inner layer 45, preferably made of what is known as a non-woven, and an outer layer made of thin plastic film (not shown), preferably made of polyethylene. Inside the inner layer, an essentially hourglass-shaped absorption layer 46 is indicated, which is thin and very flexible. Leg elastic 47, 48, which is intended to close tightly around the thighs of the wearer during use of the nappy, has been arranged along the edge portion in the crotch portion.

FIG. 11 shows diagrammatically a stiffening and at the same time absorbent element 6 of the same type as in the illustrative embodiments described above. The components corresponding to similar parts in the illustrative embodiments described above have been provided with the same reference numbers in FIG. 11. The stiffening absorbent element is anatomically adapted in the same manner as in the illustrative embodiments described above, with a dimension M adapted to the distance between said muscle tendons directly in front of the groins and with a crotch length G adapted to the crotch length of the wearer and with angles and geometry also as described above.

The embodiment of a nappy shown in FIG. 11 has a superior fit compared with conventional nappies. The presence of the stiffening element means that, when the nappy is put on, it is guided into the correct position on the wearer and that it remains in this position during use of the product.

In all the illustrative embodiments described above, the width of the stiffening element and at the same time absorbent element 6 increases continuously from the transition 12 between the front portion 1 and the crotch portion 3 to the transition area 20 between the crotch portion 3 and the rear portion. One reason for this is that the available space between the legs of the wearer is very limited and it is important to utilize the width of this area optimally. The width can increase in the order of 1.5 times between the transition 12 and the transition area 20 without the wearer finding it uncomfortable. Another reason is that the product is more stable on the wearer when the stiffening element is made as wide as possible along the crotch portion.

The invention is not limited to the illustrative embodiments described above, but a large number of modifications are possible within the scope of the patent claims below.

For example, anatomically shaped stiffening and absorbent elements of the type described above can be arranged in what are known as nappy pants, that is to say where the nappy is integrated into disposable pants.

It has been stated above that the stiffening absorbent element can be made from different materials and from laminates or one or more material(s). The stiffening absorbent element can also be made from more than one layer and with the extent of the individual layers being different, in which way it is possible for different areas of the stiffening element to have different stiffness.

As mentioned above, the stiffening element can consist of all the material layers and bonding agents included. Different stiffness in different areas of the stiffening element can therefore also be obtained by varying the degree of connection in different areas, for example different quantities of adhesive in different areas and even the absence of adhesive or other bonding agent in different areas between or in individual layers.

The weight per unit area of the stiffening element produced from a dry-formed fiber mat is not limited to the order of 100–400 g/m², but other weights per unit area are possible within the scope of the invention.

The elastic means 16, which is arranged in the cutout 13, has been indicated in the illustrative embodiments described above as having been arranged in a pretensioned state. However, in the manufacture of absorbent products such as sanitary towels, nappies and the like, it is known to arrange a heat-sensitive elastic means in an untensioned state and tension the elastic by heat treatment. This usually takes place when the articles are packed.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. An absorbent product comprising a longitudinal direction and a transverse direction, a front portion, a rear portion, a crotch portion located between the rear portion and the front portion, an absorbent element, a liquidtight layer and a stiffening element which contributes to a three-dimensional shape of the product during its use, wherein the stiffening element is in a planar state before use of the product, the stiffening element extends in the longitudinal direction of the product over the crotch portion and at least a part of the front portion, the stiffening element has a width at the transition between the crotch portion and the front portion which is substantially adapted to a distance between the muscle tendons of the wearer on both sides of the crotch of the wearer in the groin of the latter and which is about 15–45 mm, and the stiffening element extends in part over the rear portion and at the rear portion the stiffening element comprises two separate portions, one on each side of a longitudinal center line, wherein the absorbent element and the stiffening element may be the same structure or separate structures.

wherein the stiffening element comprises a dry-formed fiber mat with a density between 0.15 and 0.75 g/cm³ and a weight per unit area of about 100–400 g/m².

2. The product according to claim 1, wherein the stiffening element is absorbent and at the same time constitutes the absorbent element, and the stiffening element swells during absorption while on the whole retaining its geometry in the transverse direction of the product.

3. The product according to claim 1, wherein the width (M) of the stiffening element at the transition between the crotch portion and the front portion is 20–35 mm.

4. The absorbent product according to claim 1, wherein the side edges of the stiffening element in the front portion of the product diverge in a direction from the crotch portion toward the front portion, and the side edges of the stiffening element, in the direction from the crotch area toward the front portion, form an acute angle with a line in the longitudinal direction of the product.

5. The product according to claim 1, wherein the stiffening element has a stiffness in the dry state of in the order of 1–15 N measured according to ASTM D 4032-82.

6. The product according to claim 1, wherein the dry-formed fiber mat is, after compression, mechanically softened.

7. The product according to claim 6, wherein the dry-formed fiber mat is imparted a desired reduced stiffness and a desired extensibility by virtue of a degree of compression selected and a compression pattern selected.

8. The product according to claim 1, wherein the stiffening element has different stiffness in different areas.

9. The product according to claim 8, wherein the stiffness of the stiffening element is greater in the crotch portion than in the rear portion.

10. The product according to claim 8, wherein the side edges of the stiffening element in the front portion, which side edges diverge from the crotch portion over the front portion of the product, are arranged so as to form an angle between a line in the longitudinal direction of the product and each of said side edges of in the order of 35–55$_C$.

11. The product according to claim 10, wherein the angle is about 45°.

12. The product according to claim 1, wherein the side edges of the stiffening element in the rear portion, in the direction from the crotch portion, diverge at least some way from the crotch portion over the rear portion of the product.

13. The product according to claim 1, wherein in the rear portion, the stiffening element has a cutout extending from an end edge of the element in the direction of the crotch portion, as a result of which the product is during use imparted a fold along the longitudinal direction of the product in said cutout, which fold is adapted to extend into the cleft between the buttocks of the wearer during use of the product.

14. The product according to claim 13, wherein the cutout is wedge-shaped and symmetrically located and forms an angle of between 10$_C$ and 120$_C$ at its end facing the crotch portion.

15. The product according to claim 14, wherein the angle of the cutout is between 15° and 40°.

16. The product according to claim 1, wherein the stiffening element constitutes the absorbent element, and the stiffening element has a stiffness of at least 1.0 N according to ASTM D 4032-82, and the stiffening element is designed with essentially the same stiffness over the entire extent of the stiffening element.

17. The product according to claim 1, wherein a hump-forming element made of a resilient material is arranged under the absorbent element over at least a part of the crotch portion, which hump-forming element is arranged so as to bring about a raised portion on the side which is adapted to be fitted against the wearer, the raised portion being arranged so as to lie directly in front of the genitals of the wearer after fitting of the product on the wearer.

18. The product according to claim 17, wherein the raised portion is elongate in the longitudinal direction of the product and has a length of between 20 mm and 120 mm.

19. The product according to claim 17, wherein the raised portion is narrower than the product as a whole in the crotch area, and the raised portion is at least twice as thick as the surrounding areas.

20. The product according to claim 1, wherein an elastic is arranged in the longitudinal direction of the product and centrally along the rear portion of the product and at least along a part thereof from the crotch portion, which elastic means is intended, along its length, to draw adjacent material portions together and curve the product upwards for better contact with the body of the wearer.

21. A product according to claim 1, wherein the stiffening element serves as an absorbent and has very great liquid-spreading capacity for spreading bodily fluid received in the relatively narrow crotch area bounded by the anatomy of the wearer directly in front of the genitals of the wearer over the absorbent portions of the whole product, and the stiffening element is designed with great swelling capacity in the depth direction and attendant great absorption capacity.

22. The product according to claim 1, wherein the stiffening element serves as the absorption element and is essentially homogeneous over its entire extent with regard to thickness, stiffness, spreading capacity and absorption capacity, as a result of which the stiffening layer and thus also the absorption element curve evenly during use without forming local irregularities which may give rise to undesirable spreading of liquid.

23. The product according to claim 1, wherein a length of said transition between the crotch portion and the front portion, in which the width of the stiffening element is adapted to the distance between the muscle tendons of the wearer on both sides of the crotch of the wearer in the groin of the latter, is about 5–15 mm.

24. The product according to claim 23, wherein the stiffening element constitutes the absorbent element, and the width of the stiffening element after said transition area increases continuously in the crotch portion in the backward direction towards the rear portion for the purpose of optimally utilizing available width space in this area with regard to maximum absorption.

25. The product according to claim 1, wherein the product is arranged so as, by virtue of the stiffness selected for the stiffening element and by virtue of the selection of said geometry and dimensions in and around the transition between the crotch portion and the front portion, when the product is positioned in connection with it being put on with the transition between the front portion and the crotch portion between said muscle tendons, to be fixed in between these and in this way be transformed from plane form to three-dimensional form with the front portion curved upwards in relation to the crotch portion and forming a bowl-like shape at least in an area next to the crotch portion.

26. An absorbent product comprising a longitudinal direction and a transverse direction, a front portion, a rear portion, a crotch portion located between the rear portion and the front portion, an absorbent element, a liquidtight layer and a stiffening element which contributes to a three-dimensional shape of the product during its use, wherein the stiffening element is in a planar state before use of the product, the stiffening element extends in the longitudinal direction of the product over the crotch portion and at least a part of the front portion, the stiffening element has a width at the transition between the crotch portion and the front portion which is substantially adapted to a distance between the muscle tendons of the wearer on both sides of the crotch of the wearer in the groin of the latter and which is about 15–45 mm, and the stiffening element extends in part over the rear portion and at the rear portion the stiffening element comprises two separate portions, one on each side of a longitudinal center line, wherein the absorbent element and the stiffening element may be the same structure or separate structures, wherein the crotch portion has a length of about 70–120 mm.

* * * * *